(12) United States Patent
Bontus (10) Patent No.: US 7,627,081 B2
(45) Date of Patent: Dec. 1, 2009

(54) COMPUTER TOMOGRAPHY APPARATUS WITH MULTIPLE X-RAY RADIATION SOURCES

(75) Inventor: Claas Bontus, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 164 days.

(21) Appl. No.: 11/817,031

(22) PCT Filed: Feb. 20, 2006

(86) PCT No.: PCT/IB2006/050546
§ 371 (c)(1),
(2), (4) Date: Aug. 24, 2007

(87) PCT Pub. No.: WO2006/090323
PCT Pub. Date: Aug. 31, 2006

(65) Prior Publication Data
US 2008/0260093 A1 Oct. 23, 2008

(30) Foreign Application Priority Data
Feb. 24, 2005 (EP) .................................. 05101411

(51) Int. Cl.
*H05G 1/00* (2006.01)
*H05G 1/02* (2006.01)
(52) U.S. Cl. ............................................. 378/9; 378/4
(58) Field of Classification Search ............... 378/4–20, 378/92, 210
See application file for complete search history.

(56) References Cited
U.S. PATENT DOCUMENTS

| | | | | |
|---|---|---|---|---|
| 4,239,972 A * | 12/1980 | Wagner | ........................ | 378/9 |
| 5,068,882 A * | 11/1991 | Eberhard | ........................ | 378/4 |
| 5,440,608 A * | 8/1995 | Peralta et al. | ................ | 378/199 |
| 5,604,778 A * | 2/1997 | Polacin et al. | .................. | 378/9 |
| 5,625,661 A | 4/1997 | Oikawa | | |
| 5,966,422 A | 10/1999 | Dafni et al. | | |
| 6,208,706 B1 * | 3/2001 | Campbell et al. | .............. | 378/9 |
| 6,236,709 B1 | 5/2001 | Perry et al. | | |
| 6,760,399 B2 * | 7/2004 | Malamud | ........................ | 378/9 |
| 7,397,887 B2 * | 7/2008 | Kuhn | .............................. | 378/9 |
| 7,453,976 B1 * | 11/2008 | Yin | ................................. | 378/9 |
| 2003/0048868 A1 * | 3/2003 | Bailey et al. | .................. | 378/65 |
| 2003/0076927 A1 * | 4/2003 | Nakashima et al. | ........... | 378/65 |
| 2003/0108146 A1 | 6/2003 | Malamud | | |
| 2004/0017888 A1 * | 1/2004 | Seppi et al. | .................... | 378/57 |
| 2005/0281371 A1 * | 12/2005 | Popescu | ...................... | 378/19 |
| 2006/0045234 A1 * | 3/2006 | Pelc et al. | ....................... | 378/9 |

FOREIGN PATENT DOCUMENTS

| | | |
|---|---|---|
| EP | 1005257 A2 | 5/2000 |
| WO | 2004080310 A1 | 9/2004 |

\* cited by examiner

*Primary Examiner*—Edward J Glick
*Assistant Examiner*—Anastasia Midkiff (57) ABSTRACT

A computer tomography apparatus (100) for examination of an object of interest (107), the computer tomography apparatus (100) comprising a first electromagnetic radiation source (104) adapted to emit electromagnetic radiation to an object of interest (107), a second electromagnetic radiation source (203) adapted to emit electromagnetic radiation to the object of interest (107), at least one detecting device (108) adapted to detect electromagnetic radiation generated by the first electromagnetic radiation source (104) and by the second electromagnetic radiation source (203) and scattered on the object of interest (107), and a determination unit (118) adapted to determine structural information concerning the object of interest (107) based on an analysis of detecting signals received from the at least one detecting device (108).

18 Claims, 4 Drawing Sheets

COMPUTER TOMOGRAPHY APPARATUS WITH MULTIPLE X-RAY RADIATION SOURCES

The invention relates to the field of X-ray imaging. In particular, the invention relates to a computer tomography apparatus, to a method of examining an object of interest, to a computer-readable medium and to a program element.

Over the past several years, X-ray baggage inspections have evolved from simple X-ray imaging systems that were completely dependent on an interaction by an operator to more sophisticated automatic systems that can automatically recognize certain types of materials and trigger an alarm in the presence of dangerous materials. An inspection system has employed an X-ray radiation source for emitting X-rays which are transmitted through or scattered from the examined package to a detector.

Computed tomography (CT) is a process of using digital processing to generate a three-dimensional image of the internals of an object from a series of two-dimensional X-ray images taken around a single axis of rotation. The reconstruction of CT images can be done by applying appropriate algorithms.

Conventionally, an X-ray source and a detector are mounted on a gantry and are rotated around an object of interest in, e.g., a helical manner.

Following the trend of an increasing number of detector rows, circular computer tomography is getting more and more attractive. According to circular computer tomography, an X-ray source and a detector are mounted on a gantry and are rotated around an object of interest in a circular manner. When the detector area of a multi-row detector is large enough to cover the complete object of interest, circular scanning becomes more and more attractive compared to a helical scan as performed in many today's available computer tomography apparatuses.

However, a cone-beam reconstruction of a circular scan may introduce undesired artifacts in the reconstructed image due to the fact that the measured data are mathematically incomplete. Particularly, circular CT tends to show artifacts for slices relatively far-off the center. A reason for these artifacts is the mathematically incomplete trajectory of a circular scan, that is to say data are missing which would be needed for a more accurate reconstruction. It is unlikely that a reconstruction algorithm could ever overcome this problem.

There is a need for an imaging system in which artifacts are efficiently suppressed.

This may be achieved by a computer tomography apparatus, by a method of examining an object of interest, by a computer-readable medium and by a program element with the features according to the independent claims.

According to an exemplary embodiment of the invention, a computer tomography apparatus for examination of an object of interest is provided, comprising a first electromagnetic radiation source adapted to emit electromagnetic radiation to an object of interest, a second electromagnetic radiation source adapted to emit electromagnetic radiation to the object of interest, and at least one detecting device adapted to detect electromagnetic radiation generated by the first electromagnetic radiation source and by the second electromagnetic radiation source and scattered on the object of interest. Further, the computer tomography apparatus comprises a determination unit adapted to determine structural information concerning the object of interest based on an analysis of detecting signals received from the at least one detecting device.

According to another exemplary embodiment of the invention, a method of examining an object of interest is provided, comprising the steps of emitting electromagnetic radiation by a first electromagnetic radiation source to an object of interest, emitting electromagnetic radiation by a second electromagnetic radiation source to the object of interest, detecting electromagnetic radiation generated by the first electromagnetic radiation source and by the second electromagnetic radiation source and scattered on the object of interest, and determining structural information concerning the object of interest based on an analysis of the detected electromagnetic radiation.

Moreover, a computer-readable medium is provided according to another exemplary embodiment of the invention, in which a computer program of examining an object of interest is stored which, when being executed by a processor, is adapted to carry out the above-mentioned method steps.

Moreover, a program element of examining an object of interest is provided according to another exemplary embodiment of the invention, which program element, when being executed by a processor, is adapted to carry out the above-mentioned method steps.

The system of the invention can be realized by a computer program, i.e. by software, or by using one or more special electronic optimization circuits, i.e. in hardware, or in hybrid form, i.e. by means of software components and hardware components. The computer-readable medium and the program element may be implemented in a control system for controlling a computer tomography apparatus.

The characterizing features according to the invention particularly have the advantage that, in a scenario in which the detection signals resulting from electromagnetic radiation originating from the first electromagnetic radiation source and scattered on the object of interest do not contain sufficient information to reconstruct the structure of the object of interest, additional measurement data can be provided by the second electromagnetic radiation source, thus delivering the missing information required for a proper reconstruction of the three-dimensional structure of the object of interest.

Since the detection signals which go back to the second electromagnetic radiation source may be used supplementary and only to an extent as required for closing the gap of lacking detection data, only a minimum amount of detection information has to be captured and analyzed yielding a short reconstruction time. Further, the quality or performance offered by the second electromagnetic radiation source may be relatively low, since only additional information are provided which does not require to provide a high-end radiation source. For instance, the supplementary use of the additional radiation source makes an expensive cooling device dispensable for the additional radiation source.

The system of the invention can be implemented advantageously in the scenario of circular computer tomography, since the mathematically not complete detection signals of such a circular CT apparatus are completed by the additional radiation source.

According to an exemplary embodiment of the invention, the additional X-ray tube or tubes avoids or avoid artifacts in a image reconstructed in the frame of a circular CT system. With the improvement of the invention included, circular CT provides a number of benefits compared with helical CT. For instance, for cardiac CT, it is possible to acquire data over 360° in the desired heart phase. Using cone-beam CT scanners, a circular trajectory when taken alone is mathematically not complete, but according to the invention, the additional information may be taken from detection signals of electromagnetic radiation emitted by the second electromagnetic source and scattered on the object of interest. By providing the missing information, it is possible to remove artifacts in the reconstructed image which would occur without a second electromagnetic radiation source.

According to an aspect of the invention, data are used for the reconstruction of an image which are obtained by additional X-ray tubes. These additional X-ray tubes may be mounted, for example, underneath a patient's table or underneath a baggage inspection conveyor belt. In addition a conventional scanner having a detector and a tube which are mounted on a gantry and rotate on a circle, one or more additional tubes may be provided according to the invention. These tubes may be arranged on the gantry as well or may be arranged apart from the gantry. X-rays emitted by the additional tube can be detected by the same detector which also detects electromagnetic radiation originating from the conventional X-ray source located on the gantry. Alternatively, it is possible to use one or more additional detectors not mounted on the gantry and being configured to receive electromagnetic radiation originating from the additional X-ray tubes and scattered on the object of interest. For a particularly cheap solution, only a small number of additional tubes may be used which can be moved along an extension direction of an object of interest. For instance, such a tube may be arranged underneath a mounting table in a shiftable manner.

Using the additionally acquired data allows to significantly improve the image quality. Moreover, these additional data can be obtained any time during the scan. For instance, the additional data can be acquired before the scan or after the scan. It is possible to use, for the auxiliary or additional tubes, electromagnetic radiation sources which have much less advanced skills than the main electromagnetic radiation source. The X-ray power emitted by the additional tubes can be rather small. Thus, a sophisticated cooling technology which may be implemented for the main electromagnetic radiation source, may be dispensable for the additional magnetic radiation sources, since these tubes are usually turned on only for a relatively short period. Accordingly, the main detector can have good quality and performance, whereas the additional detectors do not need to fulfil high requirements.

The invention is directed mainly to a computer tomography apparatus in which radiation is detected which has been emitted by an electromagnetic radiation source and which has passed through (i.e. transmitted) an object of interest before impinging on the detector. However, the invention may also be applied to a computer tomography apparatus in which radiation is detected which has been emitted by an electromagnetic radiation source and which has been (coherently) scattered on an object of interest before impinging on the detector. Thus, the invention may be implemented to improve a conventional CT apparatus, or may be implemented as well in the frame of a CSCT apparatus. Consequently, the term "scatter" in the frame of the invention covers both an (incoherent) transmission of radiation passing through the object of interest and radiation which is coherently scattered by the object of interest.

Referring to the dependent claims, further exemplary embodiments of the invention will be described.

In the following, exemplary embodiments of the computer tomography apparatus of the invention will be described. However, these embodiments apply also for the method of examining an object of interest, for the computer-readable medium and for the program element.

According to one embodiment of the computer tomography apparatus, a single detecting device may be provided as a common detecting device adapted to detect electromagnetic radiation generated by the first electromagnetic radiation source and by the second electromagnetic radiation source and scattered on the object of interest. Thus, a single detecting device may be implemented for detecting both the radiation generated by the first and by the second electromagnetic radiation source. For instance, electromagnetic radiation emitted by the two electromagnetic radiation sources can be detected subsequently or simultaneously. The single detecting device may be arranged on a rotatable gantry, as well as the first electromagnetic radiation source. The second electromagnetic radiation source may either be provided on the rotatable gantry as well, or may be provided separately from the gantry. In the latter case, the gantry should not rotate when the detecting device detects electromagnetic radiation originating from the second electromagnetic radiation source.

The at least one detecting device may comprise a first detecting device adapted to detect electromagnetic radiation generated by the first electromagnetic radiation source and scattered on the object of interest, and a second detecting device adapted to detect electromagnetic radiation generated by the second electromagnetic radiation source and scattered on the object of interest. According to this embodiment, two separate detectors are provided, the first one for detecting electromagnetic radiation from a first or main source, and the other one for detecting electromagnetic radiation originating from a second or auxiliary electromagnetic radiation source. Separating the two detecting devices from each other allows a simplified assignment of detection signals to one of the two detecting devices. However, preferably, only one of the electromagnetic radiation sources emits an electromagnetic radiation at a time, so that an undesired interference of detection signals is securely avoided.

The computer tomography apparatus may be adapted such that detecting signals originating from electromagnetic radiation emitted by exactly one of the first electromagnetic radiation source and the second electromagnetic radiation source and scattered on the object of interest is insufficient to determine structural information concerning the object of interest, and that detecting signals based on electromagnetic radiation emitted by both the first electromagnetic radiation source and the second electromagnetic radiation source and scattered on the object of interest is sufficient to determine structural information concerning the object of interest. In other words, a mathematically incomplete trajectory measured by one of the electromagnetic radiation sources is completed according to the invention by the detection of additional detection signals so that all relevant information can be collected which is needed to reconstruct the three-dimensional image of the object of interest.

The computer tomography apparatus according to the invention may comprise a rotatable gantry on which the first electromagnetic radiation source and/or the second electromagnetic radiation source and at least one of the at least one detecting devices are mounted, wherein the object of interest is arrangable such that the first electromagnetic radiation source and/or the second electromagnetic radiation source and at least one of the at least one detecting device mounted on the gantry may rotate around the object of interest when the gantry is rotated. Thus, a part of the components of the computer tomography apparatus may be mounted on a rotatable gantry which rotates around an object of interest to acquire a plurality of data sets required for reconstructing the three-dimensional image of the object of interest. However, not all elements have to be mounted on the rotatable gantry. Alternatively, a part of the electromagnetic radiation sources and/or a part of the detecting devices may be arranged stationary and apart from the gantry. This allows to simplify the construction of the computer tomography apparatus, since it reduces the number of moving parts.

The rotatable gantry may be adapted to rotate the first electromagnetic radiation source and/or the second electromagnetic radiation source and at least one of the at least one detecting device mounted on the gantry in a circular manner around the object of interest. Although it is also possible that the rotation of the gantry is helical, a circular rotation trajectory is particularly advantageous, since this allows to acquire data over 360° in a desired heart phase, for instance in the frame of a cardiac CT implementation. Problems according to the state of the art related to the fact that the detection signals of a circular CT scan may be mathematically incomplete are removed by the invention, since missing signals are provided by the additional source.

In the computer tomography apparatus, the first electromagnetic radiation source may have a lower quality/offer a lower performance than the second electromagnetic radiation source. For instance, the first or main electromagnetic radiation source may be realized as a high quality source. For the second or auxiliary electromagnetic radiation source or sources, it may be sufficient to use a tube of lower quality to achieve a cost-efficient computer tomography apparatus.

In the case of the computer tomography apparatus, the first detecting device may have a lower quality/offer a lower performance than the second detecting device. Again, the first or main detecting device should have a sufficiently high quality, whereas the second or auxiliary detecting device may have a lower quality.

For instance, a scintillation counter may be used as first detecting device, whereas a semiconductor detector or another relatively cheap detector may be sufficient for the second or further detection devices.

The computer tomography apparatus according to the invention may comprise a cooling device adapted to cool the first electromagnetic radiation source, wherein the second electromagnetic radiation source may be operated without being cooled by a cooling device. According to this embodiment, a cooling device (like a water cooling device) may be provided for the first electromagnetic radiation source which is the main electromagnetic radiation source and which may become quite hot without cooling, since this tube is usually operated for a long time. However, the auxiliary radiation sources are preferably only used additionally and for a short period of time so that it is usually dispensable to provide a costly cooling device for these additional electromagnetic radiation sources as well.

The computer tomography apparatus according to the invention may comprise a mounting device on which the object of interest may be arranged. Such a mounting device may be a conveyor belt for a baggage inspection system or an operation table on which a patient under examination can be placed.

The first electromagnetic radiation source of the computer tomography apparatus may be mounted on the gantry, and the second electromagnetic radiation source may be divided into a plurality of sub-devices being mounted fixed or stationary with respect to the mounting device. According to this embodiment, only one of the electromagnetic radiation sources has to be implemented as a rotating element, whereas the additional electromagnetic radiation source or sources may be provided in a fixed manner, for instance above or below a mounting device, or integrated therein.

The first electromagnetic radiation source may be mounted on the gantry, and the second electromagnetic radiation source may be mounted linearly movable with respect to the mounting device. According to this embodiment, the first electromagnetic radiation source and the detector are provided on the gantry, whereas the additional electromagnetic radiation source or sources is or are provided in a shiftable manner above or below a patient under examination or a baggage arranged on a conveyor belt. By providing the second electromagnetic radiation source flexibly movable to a position from where a beam shall be emitted, it is possible to reduce the costs.

The at least one detecting device may be a single-slice detector. According to this embodiment, the missing information for reconstructing the 3D image may be provided by further detection elements and/or at least one further electromagnetic radiation source.

Alternatively, the at least one detecting device may be a multi-slice detector. This configuration is particularly advantageous in the frame of a circular CT apparatus, since a multi-slice detector may be configured to collect sufficient information to reconstruct structural information of an object of interest, when being completed by additional information from the at least one further electromagnetic radiation source.

The computer tomography apparatus according to the invention may be configured as one of the group consisting of a baggage inspection apparatus, a medical application apparatus, a material testing apparatus and a material science analysis apparatus. However, the computer tomography apparatus according to the invention is not restricted to the described applications, any other application may be used as well.

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited.

Figure 1:
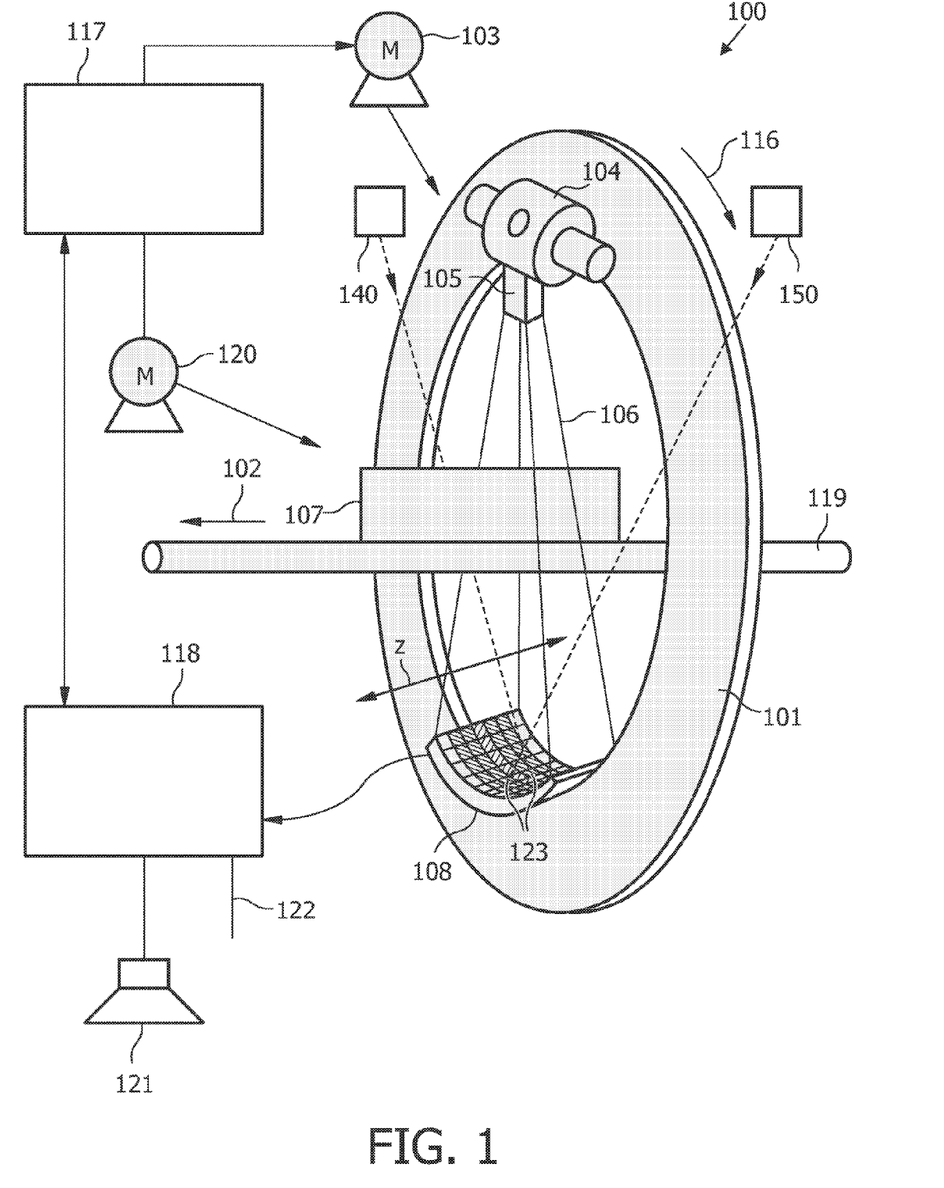
FIG. 1 shows a computer tomography apparatus according to a first embodiment of the invention.

FIG. 1 shows an exemplary embodiment of a computed tomography scanner system according to the present invention.

With reference to this exemplary embodiment, the present invention will be described for the application in baggage inspection to detect hazardous materials, such as explosives, in items of baggage. However, it should be noted that the present invention is not limited to this application, but may also be applied in the field of medical imaging, or other industrial applications such as material testing.

The computer tomography apparatus 100 depicted in FIG. 1 is a cone-beam CT scanner. However, the invention may also be carried out with a fan-beam geometry. The CT scanner depicted in FIG. 1 comprises a gantry 101, which is rotatable around a rotational axis 102. The gantry 101 is driven by means of a motor 103. Reference numeral 104 designates a main source of radiation such as an X-ray source, which, according to an aspect of the present invention, emits polychromatic or monochromatic radiation.

Reference numeral 105 designates an aperture system which forms the radiation beam emitted from the radiation source to a cone-shaped radiation beam 106. The cone-beam 106 is directed such that it penetrates an object of interest 107 arranged in the center of the gantry 101, i.e. in an examination region of the CT scanner, and impinges onto the detector 108. As may be taken from FIG. 1, the detector 108 is arranged on the gantry 101 opposite to the main source of radiation 104, such that the surface of the detector 108 is covered by the cone beam 106. The detector 108 depicted in FIG. 1 comprises a plurality of detector elements 123 each capable of detecting, in an energy-resolving manner or in a non-energy-resolving manner, X-rays which have been scattered by the object of interest 107.

During a scan of the object of interest 107, the source of radiation 104, the aperture system 105 and the detector 108 are rotated along the gantry 101 in the direction indicated by an arrow 116. For rotation of the gantry 101 with the source of radiation 104, the aperture system 105 and the detector 108, the motor 103 is connected to a motor control unit 117, which is connected to a calculation or determination unit 118.

In FIG. 1, the object of interest 107 is an item of baggage which is disposed on a conveyor belt 119. During the scan of the object of interest 107, while the gantry 101 rotates around the item of baggage 107, the conveyor belt 119 may or may not displace the object of interest 107 along a direction parallel to the rotational axis 102 of the gantry 101. By this, the object of interest 107 is scanned along a circular scan path (when the conveyor belt 119 does not displace the object of interest 107) or along a helical scan path (when the conveyor belt 119 does displace the object of interest 107). The conveyor belt 119 may be stationary or may move and may also be stopped during the scans to thereby measure signal slices. Instead of providing a conveyor belt 119, for example in medical applications where the object of interest 107 is a patient, a moveable table is used. However, it should be noted that in all of the described cases it is also possible to perform a helical scan, where there is a displacement in a direction parallel to the rotational axis 102, and additionally the rotation of the gantry 101 around the rotational axis 102. Alternatively, in all of the described cases it is also possible to perform a circular scan, where there is no displacement in a direction parallel to the rotational axis 102, but only the rotation of the gantry 101 around the rotational axis 102.

Further, it shall be emphasized that, as an alternative to the cone-beam configuration shown in FIG. 1, the invention can be realized by a fan-beam configuration. In order to generate a primary fan-beam, the aperture system 105 can be configured as a slit collimator.

The detector 108 is connected to the determination unit 118. The determination unit 118 receives the detection result, i.e. the read-outs from the detector elements 123 of the detector 108 and determines a scanning result on the basis of these read-outs. Furthermore, the determination unit 118 communicates with the motor control unit 117 in order to coordinate the movement of the gantry 101 with motors 103 and 120 with the conveyor belt 119.

The determination unit 118 is adapted for reconstructing an image from read-outs of the detector 108. A reconstructed image generated by the calculation unit 118 may be output to a display (not shown in FIG. 1) via an interface 122.

The determination unit 118 may be realized by a data processor to process read-outs from the detector elements 123 of the detector 108.

Furthermore, as may be taken from FIG. 1, the determination unit 118 may be connected to a loudspeaker 121, for example to automatically output an alarm in case of the detection of suspicious material in the item of baggage 107.

The computer tomography apparatus 100 for examination of the object of interest 107 includes the detector 108 having the plurality of detecting elements 123 arranged in a matrix-like manner, each being adapted to detect X-rays passing through the object of interest 107. Further, the computer tomography apparatus 100 comprises the determination unit 118 adapted to determine structural information concerning the object of interest 107 based on an analysis of detecting signals received from the detecting elements 123.

The computer tomography apparatus 100 comprises the main X-ray source 104 adapted to emit X-rays to the object of interest 107. The collimator 105 provided between the electromagnetic radiation source 104 and the detecting elements 123 is adapted to collimate an electromagnetic radiation beam emitted from the electromagnetic radiation source 104 to form a cone-beam. Alternatively, not shown in FIG. 1, a slit collimator can be used instead of collimator 105 to produce a fan-beam. The detecting elements 123 form a multi-slice detector array 108. The computer tomography apparatus 100 is configured as a baggage inspection apparatus.

The computer tomography apparatus 100 for examination an object of interest 107 comprises in addition to the main or first electromagnetic radiation source 104 a first auxiliary electromagnetic radiation source 140 and a second auxiliary electromagnetic radiation source 150 both being adapted as X-ray tubes to emit electromagnetic radiation to the object of interest 107. The detector 108 is further adapted to detect electromagnetic radiation generated by the main electromagnetic radiation source 104 or generated by the auxiliary electromagnetic radiation sources 140, 150 and scattered on the object of interest 107. The determination unit 108 is adapted to determine structural information concerning the object of interest 107 based on an analysis of detecting signal received from the detecting device 108.

According to the described embodiment, a single detecting device 108 is provided as a common detecting device adapted to detect electromagnetic radiation generated by the electromagnetic radiation sources 104, 140, 150 and scattered on the object of interest 107.

When a circular CT scan is performed with the computer tomography apparatus 100, detecting signals based on scattered electromagnetic radiation emitted by the main electromagnetic radiation source 104 when taken alone is insufficient to determine detailed structural information concerning the object of interest 107. However, detecting signals based on electromagnetic radiation emitted by all electromagnetic radiation source 104, 140, 150 and scattered on the object of interest 107 provides a sufficient amount of data to determine structural information concerning the object of interest 107. In other words, the mathematically incomplete trajectory of the circular rotated electromagnetic radiation source 104 is completed by additional detecting signals generated by electromagnetic radiation emitted from the fixed auxiliary electromagnetic radiation sources 140, 150 and scattered on the object of interest 107.

The first electromagnetic radiation source 104 is a high-end device offering a high level of functionality. However, the auxiliary electromagnetic radiation sources 140, 150 are low-end device offering only a low level of functionality. Such a low level of functionality is sufficient for the auxiliary electromagnetic radiation sources 140, 150, since they are only needed additionally to emit electromagnetic radiation to complete the data set. Although not shown in FIG. 1, the main electromagnetic radiation source 104 is cooled by a water cooling device, whereas the auxiliary electromagnetic radiation sources 140, 150 need not be cooled.

The baggage item under inspection 107 is mounted on the conveyor belt 119 as a mounting device.

The detector 108 comprises a plurality of matrix-like arranged detecting elements 107 and is thus a multi-slice detector array having, for instance 128 or 256 detector rows.

After having carried out a pilot-scan for defining a region of interest for a subsequent main scan, the actual measurement is carried out by circularly rotating the gantry 101, whereas in addition to detection signals originating from electromagnetic radiation generated by the main electromagnetic radiation source 104, electromagnetic radiation emitted by the auxiliary electromagnetic radiation sources 140, 150 and scattered on the object of interest 107 is used to reconstruct the structure of the object of interest.

The invention is a fast system improving the quality of a scan and removing artifacts which may occur in case of a circular CT when no additional electromagnetic radiation sources 140, 150 are provided.

In the following, referring to FIG. 2, a computer tomography apparatus 200 according to a second embodiment of the invention will be described.

Figure 2:
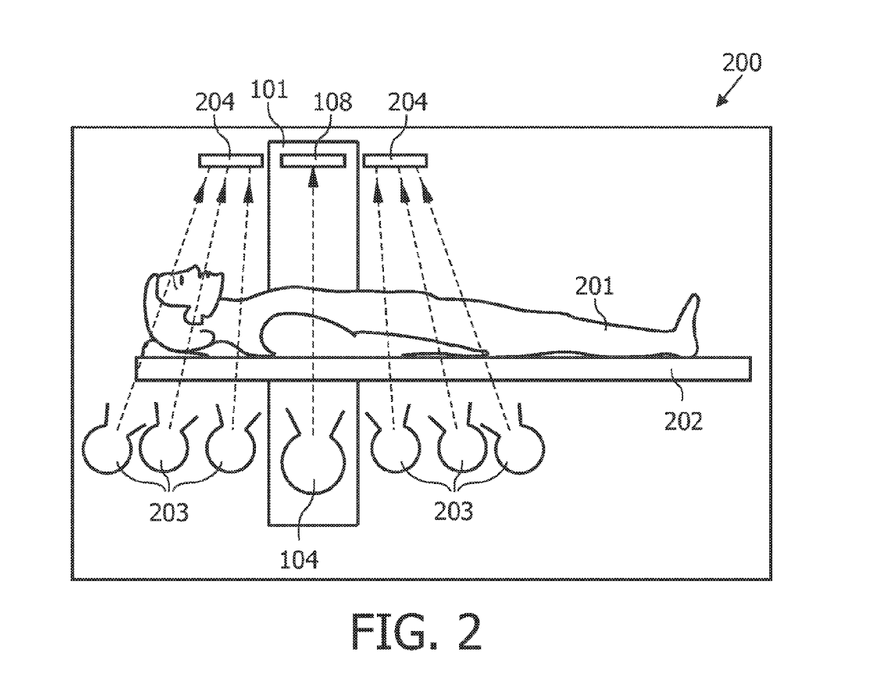
FIG. 2 shows a computer tomography apparatus according to a second embodiment of the invention.

FIG. 2 illustrates a cross-sectional view of the computer tomography apparatus 200 showing a patient 201 as an object of interest located on an examination table 202. A main electromagnetic radiation source 104 is arranged on a circularly rotatable gantry 101, as well as a detector 108. Additionally, under the operation table 202, a plurality of auxiliary X-ray tubes 203 are provided which additionally emit electromagnetic radiation impinging on the patient 201, whereas auxiliary detectors 204 are provided apart from the gantry 101 to detect electromagnetic radiation emitted by the auxiliary X-ray tubes 203 and scattered on the patient 201.

Figure 3:
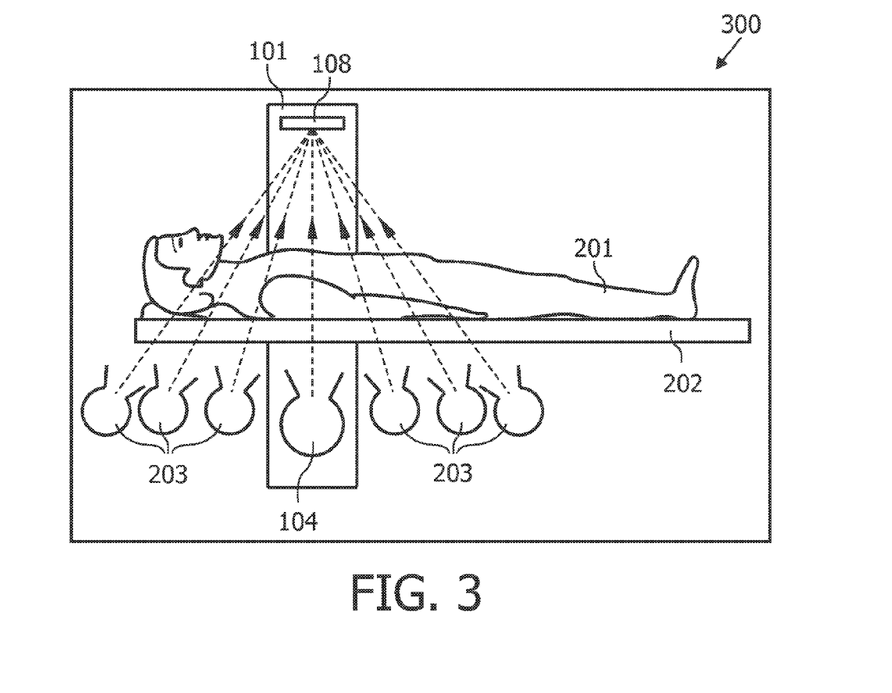
FIG. 3 shows a computer tomography apparatus according to a third embodiment of the invention.

In the following, referring to FIG. 3, a computer tomography apparatus 300 according to a third embodiment of the invention will be described.

The computer tomography apparatus 300 differs from the computer tomography apparatus 200 in that the additional detectors 204 are omitted. In contrast to this, electromagnetic radiation emitted by the auxiliary X-ray tubes 203 and scattered on the patient 201 are detected by the detector 108 which is also provided for detecting electromagnetic radiation emitted by the main X-ray tube 104 and scattered on the patient 201.

Figure 4:
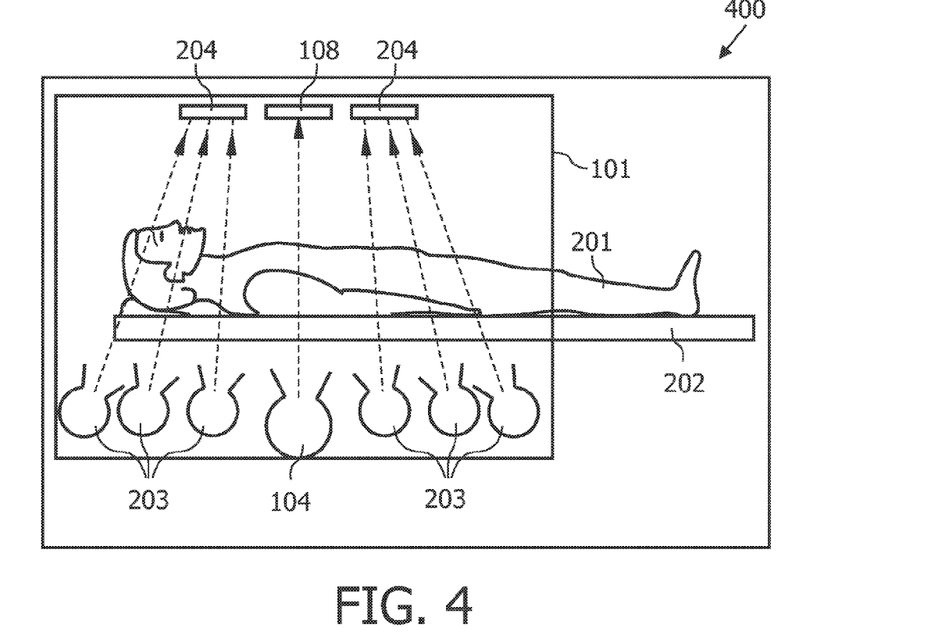
FIG. 4 shows a computer tomography apparatus according to a fourth embodiment of the invention.

In the following, referring to FIG. 4, a computer tomography apparatus 400 according to a forth embodiment of the invention will be described.

The computer tomography apparatus 400 differs from the computer tomography apparatus 200 in that also the auxiliary X-ray tubes 203 and the auxiliary detectors 204 are provided on the rotatable gantry 101.

Figure 5:
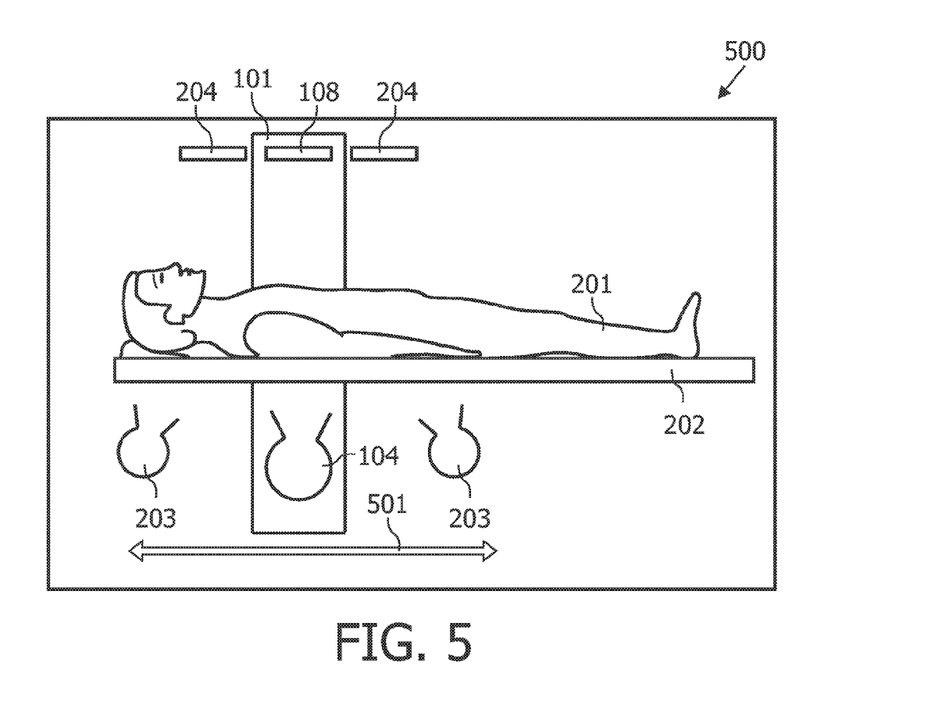
FIG. 5 shows a computer tomography apparatus according to a fifth embodiment of the invention.

In the following, referring to FIG. 5, a computer tomography apparatus 500 according to a fifth embodiment of the invention will be described.

The computer tomography apparatus 500 differs from the computer tomography apparatus 200 in that only one or two instead of six auxiliary X-ray tubes 203 are used which are provided shiftable along a direction 501 below the patient 201. The provision of the auxiliary X-ray tubes 203 in a movable manner allows to minimize the number of additional X-ray tubes.

Figure 6:
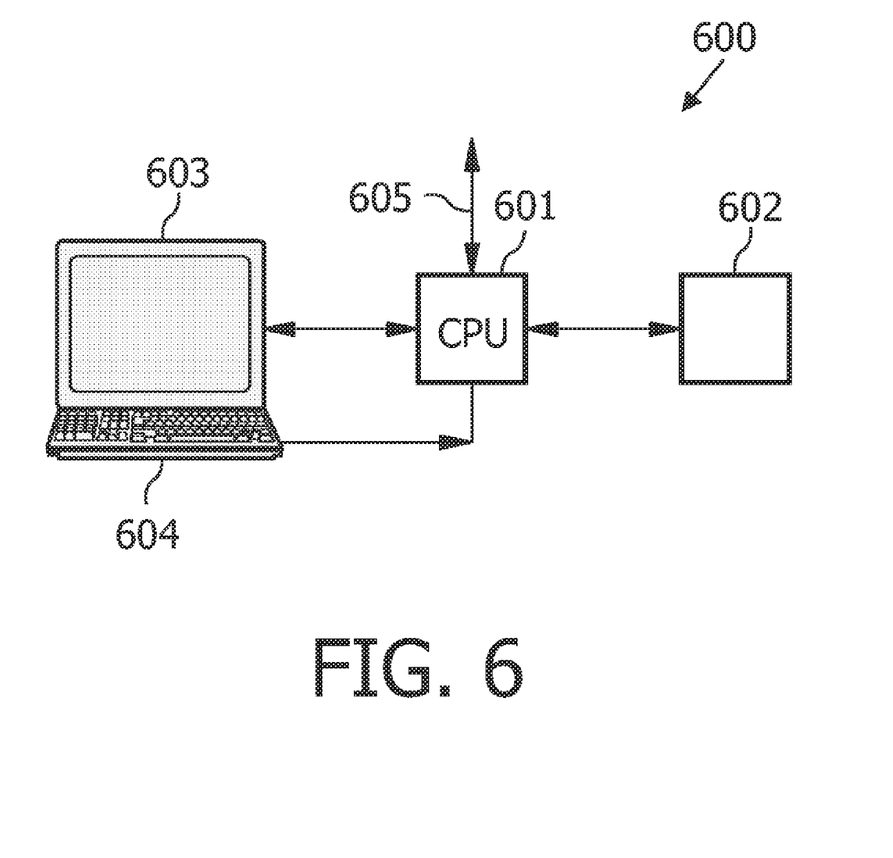
FIG. 6 shows an exemplary embodiment of a data processing device to be implemented in the computer tomography apparatus of the invention The illustration in the drawings is schematically. In different drawings, similar or identical elements are provided with the same reference signs.

FIG. 6 depicts an exemplary embodiment of a data processing device 600 according to the present invention for executing an exemplary embodiment of a method in accordance with the present invention. The data processing device 600 depicted in FIG. 6 comprises a central processing unit (CPU) or image processor 601 connected to a memory 602 for storing an image depicting an object of interest, such as a patient. The data processor 601 may be connected to a plurality of input/output network or diagnosis devices, such as an MR device or a CT device. The data processor 601 may furthermore be connected to a display device 603, for example a computer monitor, for displaying information or an image computed or adapted in the data processor 601. An operator or user may interact with the data processor 601 via a keyboard 604 and/or other output devices, which are not depicted in FIG. 6. Furthermore, via the bus system 605, it is also possible to connect the image processing and control processor 601 to, for example a motion monitor, which monitors a motion of the object of interest. In case, for example, a lung of a patient is imaged, the motion sensor may be an exhalation sensor. In case the heart is imaged, the motion sensor may be an electrocardiogram (ECG).

Exemplary technical fields, in which the present invention may be applied advantageously, include baggage inspection, medical applications, material testing, and material science. An improved image quality and less artifacts in combination with a low effort may be achieved. Also, the invention can be applied in the field of heart scanning to detect heart diseases.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

The invention claimed is:

1. A computer tomography apparatus for examination of an object of interest, the computer tomography apparatus comprising:

a mounting device configured to support an object of interest;

a rotatable gantry mounted for rotation around the mounting device;

a first electromagnetic radiation source adapted to emit electromagnetic radiation to an object of interest, the first electromagnetic radiation source being mounted on the rotatable gantry;

a second electromagnetic radiation source adapted to emit electromagnetic radiation to the object of interest, the second electromagnetic radiation source being divided into a plurality of sub-devices mounted in a fixed manner with respect to the mounting device;

at least one detecting device adapted to detect electromagnetic radiation generated by the first electromagnetic radiation source and by the second electromagnetic radiation source and scattered on the object of interest, at least one of the at least one detecting device being mounted on the rotatable gantry;

a determination unit adapted to determine structural information concerning the object of interest based on an analysis of detected signals received from the at least one detecting device; and wherein the object of interest is arrangable such that the first electromagnetic radiation source and at least one of the at least one detecting device mounted on the gantry rotate around the object of interest when the rotatable gantry is rotated.

2. The computer tomography apparatus according to claim 1, wherein a single detecting device mounted to the rotating gantry is provided as a common detecting device adapted to detect electromagnetic radiation generated by the first electromagnetic radiation source and by the second electromagnetic radiation source and scattered on the object of interest.

3. The computer tomography apparatus according to claim 1, wherein the at least one detecting device comprises:
a first detecting device mounted to the rotatable gantry to detect electromagnetic radiation generated by the first electromagnetic radiation source and scattered on the object of interest; and
a second detecting device mounted in a fixed manner relative to the mounting device to detect electromagnetic radiation generated by the second electromagnetic radiation source and scattered on the object of interest.

4. The computer tomography apparatus according to claim 1, wherein the rotatable gantry is adapted to rotate the first electromagnetic radiation source and at least one of the at least one detecting device mounted on the rotatable gantry on a circular trajectory around the object of interest.

5. The computer tomography apparatus according to claim 1, comprising a cooling device adapted to cool the first electromagnetic radiation source, wherein the second electromagnetic radiation source is not cooled by a cooling device.

6. The computer tomography apparatus according to claim 1, wherein at least one of the plurality of sub devices of the second electromagnetic radiation source is mounted linearly movable with respect to the mounting device.

7. The computer tomography apparatus according to claim 1, wherein the at least one detecting device is realized as a single-slice detecting device.

8. The computer tomography apparatus according to claim 1, wherein the at least one detecting device is realized as a multi-slice detecting device.

9. The computer tomography apparatus according to claim 1, configured as one of the group consisting of a baggage inspection apparatus, a medical application apparatus, a material testing apparatus and a material science analysis apparatus.

10. A method of examining an object of interest, the method comprising:
rotating a rotating radiation source around an object of interest;
emitting radiation by the rotating radiation source to the object of interest while the rotating radiation source is rotating;
emitting radiation by a non-rotating radiation source to the object of interest while the non-rotating radiation source is mounted non-rotatably relative to the object of interest;
detecting radiation generated by the rotating radiation source and by the non-rotating radiation source that interact with the object of interest;
determining structural information concerning the object of interest based on an analysis of the detected radiation.

11. A computer-readable medium, which carries instructions which, when being executed by a processor, controls the processor to carry out the steps of:
emitting electromagnetic radiation by a first electromagnetic radiation source rotating around an object of interest;
emitting electromagnetic radiation by a second electromagnetic radiation source non-rotatably disposed relative to the object of interest;
detecting electromagnetic radiation generated by the rotating first electromagnetic radiation source and by the non-rotating second electromagnetic radiation source interacted with the object of interest;
determining structural information concerning the object of interest based on an analysis of the detected electromagnetic radiation.

12. A program element of examining an object of interest, which, when being executed by a processor carries out the steps of:
emitting electromagnetic radiation by a rotating electromagnetic radiation source which rotates around an object of interest;
emitting electromagnetic radiation by a non-rotating electromagnetic radiation source which does not rotate around the object of interest;
detecting electromagnetic radiation generated by rotating first electromagnetic radiation source and by the non-rotating electromagnetic radiation source and scattered on the object of interest;
determining structural information concerning the object of interest based on an analysis of the detected electromagnetic radiation.

13. A computer tomography apparatus for examination of an object of interest, the computer tomography apparatus comprising:
an object support;
a rotatable gantry which rotates about the object support;
a rotatable radiation source for irradiating the object and a rotatable radiation detector for detecting radiation mounted to the rotatable gantry for rotation therewith;
a non-rotatable radiation source for irradiating the object mounted separate from the rotatable gantry.

14. The computer tomography apparatus according to claim 13, further including:
a non-rotatable radiation detector which detects radiation from the non-rotatable radiation source.

15. The computer tomography apparatus according to claim 14, wherein the non-rotatable radiation source is mounted for axial movement substantially parallel to an axis of rotation of the rotatable gantry.

16. The computer tomography apparatus according to claim 13, wherein the rotatable detector detects radiation from both the rotatable and non-rotatable radiation source and further including:
a unit which determines structural information concerning the object of interest based on radiation detected by the rotatable radiation detector.

17. The computer tomography apparatus according to claim 13, wherein the object support is configured to move the object of interest axially substantially parallel to an axis of rotation of the rotatable gantry.

18. The computer tomography apparatus according to claim 13, further including:
a second non-rotatable radiation source, the first and second non-rotatable radiation sources being disposed on opposite sides of a plane of rotation of the rotatable gantry.

* * * * *